(12) United States Patent
Bjørnvad et al.

(10) Patent No.: US 6,399,351 B1
(45) Date of Patent: Jun. 4, 2002

(54) PECTATE LYASES

(75) Inventors: Mads Eskelund Bjørnvad, Frederiksberg; Jens Toenne Andersen, Naerum; Kirk Schnorr, Copenhagen N; Martin Schülein, Copenhagen Ø; Lars Kongsbak, Holte, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/526,416

(22) Filed: Mar. 15, 2000

Related U.S. Application Data

(60) Provisional application No. 60/124,969, filed on Mar. 18, 1999.

(30) Foreign Application Priority Data

Mar. 16, 1999 (DK) ......................................... 1999 00367

(51) Int. Cl.$^7$ .......................... C12N 9/88; D06M 16/00; C07G 17/00; D21C 1/00
(52) U.S. Cl. ....................... 435/232; 435/200; 435/262; 435/263; 435/264; 435/267; 435/277; 435/278; 530/350; 510/320; 510/392; 426/599; 426/592; 426/656
(58) Field of Search ............................... 435/69.1, 183, 435/200, 262, 263, 264, 267, 232, 277, 278; 530/350; 426/599, 592, 656; 510/320, 392

(56) References Cited

FOREIGN PATENT DOCUMENTS

| EP | 0 870 834 A1 | 10/1998 |
|---|---|---|
| WO | WO 97/27290 | 7/1997 |
| WO | WO 97/27291 | 7/1997 |
| WO | WO 98/45393 | 10/1998 |
| WO | WO 99/27083 | 6/1999 |
| WO | WO 99/27084 | 6/1999 |

OTHER PUBLICATIONS

Kim et al., (1994) Biosci. Biotech. Biochem. 58(5):947–949.
Nasser et al., (1993) FEBS 335(3):319–326.
Karbassi et al., (1980) Can. J. Microbiol. 26:377–384.
Dave et al., (1971) J. of Bacteriology 108(1):166–174.
Kelly et al., (1978) Can. J. Microbiol. 24:1164–1172.
Hasegawa et al., (1966) J. Food Sci. 31:838–845.
Patent Abstracts of Japan 10–337187, Dec. 22, 1998.

*Primary Examiner*—Rebecca E. Prouty
*Assistant Examiner*—Manjunath N. Rao
(74) *Attorney, Agent, or Firm*—Elias Lambiris

(57) ABSTRACT

A novel pectate lyase belonging to a novel family of polysaccharide lyases has good performance in industrial processes under neutral or alkaline conditions such as laundering and textile processing. The pectate lyase may be derivable from Bacillus species.

26 Claims, No Drawings

SEQUENCE LISTING

<160> NUMBER OF SEQ ID NOS: 12

<210> SEQ ID NO 1
<211> LENGTH: 1035
<212> TYPE: DNA
<213> ORGANISM: Bacillus

<400> SEQUENCE: 1

```
ttgaaagcgc ttaaacgaat gtctaaactt gctatttccg gattatgtgc t ggcttttc      60
gttatgctgg cgtccacgac tgccgccgca gaagaagcaa cggtttccaa c gaaacgatc    120
attaaacaag ccaaccatct gttgacttgg caaatggacc atggcggctg g tcgaaagac   180
atgccgcaaa tgtatacgcg agactggaac ggcagggaag caaaatcggt t tggacttca   240
aatggacaag aacttggaac gattgacaat gatgccaccg tcgatgaaat t cgcgttgtt   300
gccgaagcgt accaactgac aaaagacgaa cgctttaaag caagcgtcca c aacggcatt   360
gatttccttt ataaactcca atatccgagc ggcggctttc gccaagtgta t ccacaacgg   420
ggcagcgacc cgtccagttc cgtctggtac tccaattatg tcactttaa c gaccatgcg   480
atggtcaacg tcctccgctt gcttgaagac gcccgccaag aaaagcgcc a tttggaggc   540
gacttattca acgattcaca gcgtcgggaa atggccgctt caattgaggg c ggattggat   600
tatatttac gagcccaaat cgtcgcaaac ggcaaaaaaa ccgcctgggg c caacaacat   660
gaccctgtga cgctgcaacc gcagcaagga cgtgcttatg agcatccttc g attgcaaca   720
gatgaatcgg taggcattgt ccaatggttg gaagaacagc caaaccaatc a gctgctgtc   780
cgggaagcgg tcgctgcggc acgggcgtgg atggatgaag cacgtgtcgc t gatacacgc   840
tacgaacgcc gcgtcgagcc ccatttttc catgagcctg gggcagagac a tggtatcgt   900
ttttatcaaa tcggcaccaa ccgcccgatt ttttcagggc gtgacggcgt c atccaccat   960
gacattatga acgttgaaca agaacgacgt tatggctatg cttgggctgg g aattggccg  1020
caaaagcttc gttaa                                                    1035
```

<210> SEQ ID NO 2
<211> LENGTH: 344
<212> TYPE: PRT
<213> ORGANISM: Bacillus

<400> SEQUENCE: 2

```
Met Lys Ala Leu Lys Arg Met Ser Lys Leu A la Ile Ser Gly Leu Cys
1               5                   10                  15

Ala Gly Phe Phe Val Met Leu Ala Ser Thr T hr Ala Ala Ala Glu Glu
            20                  25                  30

Ala Thr Val Ser Asn Glu Thr Ile Ile Lys G ln Ala Asn His Leu Leu
        35                  40                  45

Thr Trp Gln Met Asp His Gly Gly Trp Ser L ys Asp Met Pro Gln Met
    50                  55                  60

Tyr Thr Arg Asp Trp Asn Gly Arg Glu Ala L ys Ser Val Trp Thr Ser
65                  70                  75                  80

Asn Gly Gln Glu Leu Gly Thr Ile Asp Asn A sp Ala Thr Val Asp Glu
                85                  90                  95

Ile Arg Val Val Ala Glu Ala Tyr Gln Leu T hr Lys Asp Glu Arg Phe
            100                 105                 110

Lys Ala Ser Val His Asn Gly Ile Asp Phe L eu Tyr Lys Leu Gln Tyr
        115                 120                 125
```

```
Pro Ser Gly Gly Phe Arg Gln Val Tyr Pro Gln Arg Gly Ser Asp Pro
    130                 135                 140
Ser Ser Ser Val Trp Tyr Ser Asn Tyr Val Thr Phe Asn Asp His Ala
145                 150                 155                 160
Met Val Asn Val Leu Arg Leu Leu Glu Asp Ala Arg Gln Gly Lys Ala
                165                 170                 175
Pro Phe Gly Gly Asp Leu Phe Asn Asp Ser Gln Arg Arg Glu Met Ala
            180                 185                 190
Ala Ser Ile Glu Gly Gly Leu Asp Tyr Ile Leu Arg Ala Gln Ile Val
        195                 200                 205
Ala Asn Gly Lys Lys Thr Ala Trp Gly Gln Gln His Asp Pro Val Thr
    210                 215                 220
Leu Gln Pro Gln Gln Gly Arg Ala Tyr Glu His Pro Ser Ile Ala Thr
225                 230                 235                 240
Asp Glu Ser Val Gly Ile Val Gln Trp Leu Glu Glu Gln Pro Asn Gln
                245                 250                 255
Ser Ala Ala Val Arg Glu Ala Val Ala Ala Ala Arg Ala Trp Met Asp
            260                 265                 270
Glu Ala Arg Val Ala Asp Thr Arg Tyr Glu Arg Arg Val Glu Pro His
        275                 280                 285
Phe Phe His Glu Pro Gly Ala Glu Thr Trp Tyr Arg Phe Tyr Gln Ile
    290                 295                 300
Gly Thr Asn Arg Pro Ile Phe Ser Gly Arg Asp Gly Val Ile His His
305                 310                 315                 320
Asp Ile Met Asn Val Glu Gln Glu Arg Arg Tyr Gly Tyr Ala Trp Ala
                325                 330                 335
Gly Asn Trp Pro Gln Lys Leu Arg
            340

<210> SEQ ID NO 3
<211> LENGTH: 9
<212> TYPE: DNA
<213> ORGANISM: Artificial Sequence
<220> FEATURE:
<223> OTHER INFORMATION: Primer

<400> SEQUENCE: 3 atgcacggg                                                                 9

<210> SEQ ID NO 4
<211> LENGTH: 9
<212> TYPE: DNA
<213> ORGANISM: Artificial Sequence
<220> FEATURE:
<223> OTHER INFORMATION: Primer

<400> SEQUENCE: 4 cccgtgcat                                                                 9

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
gtcgccgggg cggccgctat caattggtaa ctgtatctca gc                           42
```

```
<210> SEQ ID NO 6
<211> LENGTH: 64
<212> TYPE: DNA
<213> ORGANISM: Artificial Sequence
<220> FEATURE:
<223> OTHER INFORMATION: Primer

<400> SEQUENCE: 6
gtcgcccggg agctctgatc aggtaccaag cttgtcgacc tgcagaatga g gcagcaaga      60 agat                                                                    64

<210> SEQ ID NO 7
<211> LENGTH: 61
<212> TYPE: DNA
<213> ORGANISM: Artificial Sequence
<220> FEATURE:
<223> OTHER INFORMATION: Primer

<400> SEQUENCE: 7
gtcggcggcc gctgatcacg taccaagctt gtcgacctgc agaatgaggc a gcaagaaga      60 t                                                                       61

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
gtcggagctc tatcaattgg taactgtatc tcagc                                  35

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
aacagctgat cacgactgat cttttagctt ggcac                                  35

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
aactgcagcc gcggcacatc ataatgggac aaatggg                                37

<210> SEQ ID NO 11
<211> LENGTH: 43
<212> TYPE: DNA
<213> ORGANISM: Artificial Sequence
<220> FEATURE:
<223> OTHER INFORMATION: Primer

<400> SEQUENCE: 11
cattctgcag ccgcggcagc agaagaagca acggtttcca acg                         43

<210> SEQ ID NO 12
<211> LENGTH: 43
```

```
-continued
<212> TYPE: DNA
<213> ORGANISM: Artificial Sequence
<220> FEATURE:
<223> OTHER INFORMATION: Primer

<400> SEQUENCE: 12
gcgttgagac gcgcggccgc tcattaacga agcttttgcg gcc                    43
```

PECTATE LYASES

CROSS-REFERENCE TO RELATED APPLICATIONS

This application claims priority under 35 U.S.C. 119 of Danish application PA 1999 00367 filed Mar. 16, 1999, and of U.S. Provisional No. 60/124,969 filed Mar. 18, 1999, the contents of which are fully incorporated herein by reference.

The present invention relates to microbial pectate lyases, more specifically to a novel subclass of pectate lyases (EC 4.2.2.2), especially to a novel family of polysaccharide lyases exhibiting pectate lyase activity, ie enzymes which are capable of eliminative cleavage of pectate to give oligosaccharides with 4-deoxy-alpha-D-gluc-4-enuronosyl groups at their non-reducing ends; to a method of producing such enzymes; and to methods for using such enzymes in the textile, detergent and cellulose fiber processing industries.

BACKGROUND OF THE INVENTION

Pectin polymers are important constituents of plant cell walls. Pectin is a hetero-polysaccharide with a backbone composed of alternating homogalacturonan (smooth regions) and rhamnogalacturonan (hairy regions). The smooth regions are linear polymers of 1,4-linked alpha-D-galacturonic acid. The galacturonic acid residues can be methyl-esterified on the carboxyl group to a varying degree, usually in a non-random fashion with blocks of polygalacturonic acid being completely methyl-esterified.

Pectinases can be classified according to their preferential substrate, highly methyl-esterified pectin or low methyl-esterified pectin and polygalacturonic acid (pectate), and their reaction mechanism, beta-elimination or hydrolysis. Pectinases can be mainly endo-acting, cutting the polymer at random sites within the chain to give a mixture of oligomers, or they may be exo-acting, attacking from one end of the polymer and producing monomers or dimers. Several pectinase activities acting on the smooth regions of pectin are included in the classification of enzymes provided by the Enzyme Nomenclature (1992) such as pectate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and exo-poly-alpha-galacturonosidase (EC 3.2.1.82).

Pectate lyases have been cloned from different bacterial genera such as Erwinia, Pseudomonas, Klebsiella and Xanthomonas. Also from *Bacillus subtilis* (Nasser et al. (1993) FEBS 335:319–326) and Bacillus sp. YA-14 (Kim et al. (1994) Biosci. Biotech. Biochem. 58:947–949) cloning of a pectate lyase has been described. Purification of pectate lyases with maximum activity in the pH range of 8–10 produced by *Bacillus pumilus* (Dave and Vaughn (1971) J. Bacteriol. 108:166–174), *B. polymyxa* (Nagel and Vaughn (1961) Arch. Biochem. Biophys. 93:344–352), *B. stearothermophilus* (Karbassi and Vaughn (1980) Can. J. Microbiol. 26:377–384), Bacillus sp. (Hasegawa and Nagel (1966) J. Food Sci. 31:838–845) and Bacillus sp. RK9 (Kelly and Fogarty (1978) Can. J. Microbiol. 24:1164–1172) has been reported, however, no publication was found on cloning of pectate lyase encoding genes from these organisms. All the pectate lyases described require divalent cations for maximum activity, calcium ions being the most stimulatory.

Polysaccharide lyases are classified into families according to their three-dimensional structure or folding; conventionally the Clustal W method is used the for family determination. Based on amino acid sequence alignment and the Clustal W method, a polypeptide or protein can be classified into a specific polysaccharide lyase family, ie either a known family or a novel and hitherto unknown family (The Sanger Centre: Protein Families Database of alignments and HMMs; www. sanger.ac.uk). At present known pectate lyases belong to polysaccharide lyase family 1, family 2 and family 9 (ExPASy-molecular biology WWW server of the Swiss Institute of Bioinformatics (SIB)).

WO 98/45393 discloses detergent compositions containing protopectinase with remarkable detergency against muddy soilings.

Generally, pectinase producing microorganisms exhibit a broad range of pectin degrading or modifying enzymes. Often the microorganisms also produce cellulases and/or hemicellulases. Complex multi-component enzyme preparations from such microorganisms may be difficult to optimise for use in various applications, a.o. since they even may contain enzymes with detrimental effect. Thus, it is an object of the present invention to provide a pectin degrading enzyme exhibiting only the desired effects e.g. in detergents, in textile processing or different industrial processes.

SUMMARY OF THE INVENTION

The inventors have now found and identified a novel enzyme having substantial pectate lyase activity which enzyme has excellent performance in various industrial processes. Further, the inventors have succeeded in identifying a DNA sequence encoding the enzyme. It was found that the novel pectate lyase enzyme is a member of a hitherto unknown class of pectate lyases, ie the present enzyme belongs to a hitherto unknown family of polysaccharide lyases. Based on the present disclosure, especially the materials, methods and sequence listings provided herein, it is contemplated that the skilled person can find and identify other members of this novel polysaccharide lyase family, preferably pectate lyases of microbial origin, especially bacterial or fungal pectate lyases.

It is believed that the novel pectate lyase enzymes will be classified according to the Enzyme Nomenclature in the Enzyme Class EC 4.2.2.2.

Accordingly, in a first aspect this invention relates to a pectate lyase enzyme belonging to a polysaccharide family other that family 1,2 and 9, which enzyme is selected from one of a) polypeptide encoded by the DNA sequence of positions 88–1033 of SEQ ID NO:1; b) a polypeptide produced by culturing a cell comprising the sequence of SEQ ID NO:1 under conditions wherein the DNA sequence is expressed; c) a pectate lyase enzyme comprising an amino acid sequence of at least 35% identity to positions 30–344 of SEQ ID NO:2 when identity is determined by GAP provided in the GCG program package using a GAP creation penalty of 3.0 and GAP extension penalty of 0.1; or d) a polypeptide encoded by the pectate lyase encoding part of the DNA sequence obtainable from the plasmid in *Escherichia coli* DSM 12712.

In a second aspect, the present invention relates to isolated pectate lyase enzyme, in which the enzyme is (i) free from homologous impurities, and (ii) produced by culturing a cell comprising the DNA sequence of positions 88–1033 of SEQ ID NO:1, wherein the enzyme is produced and isolated.

In third aspect, the invention relates to an isolated polynucleotide molecule encoding a polypeptide having pectate lyase activity selected from the group consisting of (a) polynucleotide molecules comprising a nucleotide sequence as shown in SEQ ID NO:1 from nucleotide 88 to nucleotide 1033; (b) species homologs of (a); (c) polynucleotide molecules encoding a polypeptide being at least 35% identical to the amino acid sequence of SEQ ID NO:2 from amino acid residue 30 to amino acid residue 344; (d) molecules complementary to (a), (b), or (c); (e) degenerate nucleotide sequences of (a) or (b); and (f) polynucleotide molecules encoding a polypeptide having pectate lyase activity which polynucleotide molecule hybridises to a denatured double-stranded DNA probe under medium stringency conditions, wherein the probe is selected from the group consisting of DNA probes comprising the sequence shown in positions 88–1033 of SEQ ID NO:1 and DNA probes comprising a subsequence of positions 88–1033 of SEQ ID NO:1, the subsequence having a length of at least about 100 base pairs.

In a further aspect, the present invention provides an expression vector comprising the following operably linked elements: a transcription promoter; a DNA segment selected from the group consisting of a) polynucleotide molecules encoding a polypeptide having pectate lyase activity comprising a nucleotide sequence as shown in SEQ ID NO:1 from nucleotide 88 to nucleotide 1033, b) polynucleotide molecules encoding a polypeptide having pectate lyase activity that is at least 35% identical to the amino acid sequence of SEQ ID NO:2 from amino acid residue 30 to amino acid residue 344, and (c) degenerate nucleotide sequences of (a) or (b); and a transcription terminator.

Within yet another aspect of the present invention there is provided a cultured cell into which has been introduced an expression vector as disclosed above, wherein said cell expresses the polypeptide encoded by the DNA segment.

Within another aspect of the present invention there is provided an enzyme composition or preparation comprising a purified pectate lyase according to the invention optionally in combination with other polypeptides having enzymatic activity.

Within yet another aspect of the present invention there are provided methods for producing a polypeptide according to the invention comprising culturing a cell into which has been introduced an expression vector as disclosed above, whereby said cell expresses a polypeptide encoded by the DNA segment and recovering the polypeptide.

The novel pectate lyase enzymes of the present invention are useful for the treatment of cellulosic material, especially cellulose-containing fiber, yarn, woven or non-woven fabric, treatment of mechanical paper-making pulps or recycled waste paper, and for retting of fibres. The treatment can be carried out during the processing of cellulosic material into a material ready for garment manufacture or fabric manufacture, e.g. in the desizing or scouring step; or during industrial or household laundering of such fabric or garment.

Accordingly, in further aspects the present invention relates to a detergent composition comprising an enzyme having substantial pectate lyase activity; and to use of the enzyme of the invention for the treatment of cellulose-containing fibers, yarn, woven or non-woven fabric.

The pectate lyases of the invention are very effective for use in an enzymatic scouring process in the preparation of cellulosic material e.g. for proper response in subsequent dyeing operations. Further, it is contemplated that detergent compositions comprising the novel pectate lyases are capable of removing or bleaching certain soils or stains present on laundry, especially soils and spots resulting from galactan or arabinogalactan containing food, plants, and the like. It is also contemplated that treatment with detergent compositions comprising the novel enzyme can prevent binding of certain soils to the cellulosic material. The enzymes of the invention are also useful as ingredients in hard surface cleaning compositions having the effect of removing or assisting in removing certain soils or stains from hard surfaces in need of cleaning.

DEPOSITIONS

The plasmid pSJ1678 comprising the polynucleotide molecule (the DNA sequence) encoding a pectate lyase of the present invention has been transformed into a strain of the *Escherichia coli* which was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany, on Mar. 4, 1999 under the deposition number DSM 12712.

DEFINITIONS

Prior to discussing this invention in further detail, the following terms will first be defined.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. The expression vector of the invention may be any expression vector that is conveniently subjected to recombinant DNA procedures, and the choice of vector will often depend on the host cell into which the vector it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The term "recombinant expressed" or "recombinantly expressed" used herein in connection with expression of a polypeptide or protein is defined according to the standard definition in the art. Recombinantly expression of a protein is generally performed by using an expression vector as described immediately above.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). The term "an isolated polynucleotide" may alternatively be termed "a cloned polynucleotide".

When applied to a protein/polypeptide, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a greater than 40% pure form, more preferably greater than 60% pure form.

Even more preferably it is preferred to provide the protein in a highly purified form, i.e., greater than 80% pure, more preferably greater than 95% pure, and even more preferably greater than 99% pure, as determined by SDS-PAGE.

The term "isolated protein/polypeptide may alternatively be termed "purified protein/polypeptide".

The term "homologous impurities" means any impurity (e.g. another polypeptide than the polypeptide of the invention) which originate from the homologous cell where the polypeptide of the invention is originally obtained from.

The term "obtained from" as used herein in connection with a specific microbial source, means that the polynucleotide and/or polypeptide produced by the specific source, or by a cell in which a gene from the source have been inserted.

The term "endogeneous to" as used herein in connection with a specific microbial source, means that a polypeptide is produced by the specific source due to the presence in the source of a native gene, ie a gene which has not been recombinantly inserted into a cell of the source but is naturally occurring.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' (SEQ ID NO:3) is complementary to 5' CCCGTGCAT 3' (SEQ ID NO:4).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "enzyme core" is to be understood as being the part of a single- or multi-domain structure polypeptide exhibiting enzymatic activity which part is a single domain part containing the catalytically active domain. Accordingly, the enzyme core does not contain other domains than the catalytic domain.

The term "pectin" denotes pectate, polygalacturonic acid, and pectin which may be esterified to a higher or lower degree.

The term "pectinase" denotes a pectinase enzyme defined according to the art where pectinases are a group of enzymes that cleave glycosidic linkages of pectic substances mainly poly(1,4-alpha-D-galacturonide and its derivatives(see reference Sakai et al., Pectin, pectinase and protopectinase: production, properties and applications, pp 213–294 in: Advances in Applied Microbiology vol:39, 1993).

Preferably a pectinase of the invention is a pectinase enzyme which catalyzes the random cleavage of alpha-1,4-glycosidic linkages in pectic acid also called polygalacturonic acid by transelimination such as the enzyme class polygalacturonate lyase (EC 4.2.2.2) (PGL) also known as poly(1,4-alpha-D-galacturonide) lyase also known as pectate lyase.

DETAILED DESCRIPTION OF THE INVENTION

HOW TO USE A SEQUENCE OF THE INVENTION TO GET OTHER RELATED SEQUENCES: The disclosed sequence information herein relating to a polynucleotide sequence encoding a pectate lyase of the invention can be used as a tool to identify other homologous pectate lyases, preferably pectate lyases belonging to the same novel family of polysaccharide lyases as the pectate lyase represented by the amino acid sequence of the appended SEQ ID NO:2. For instance, polymerase chain reaction (PCR) can be used to amplify sequences encoding other homologous pectate lyases from a variety of microbial sources, in particular of different Bacillus species.

POLYNUCLEOTIDES

Within preferred embodiments of the invention an isolated polynucleotide of the invention will hybridize to similar sized regions of SEQ ID No. 1 or a sequence complementary thereto, under at least medium stringency conditions.

In particular polynucleotides of the invention will hybridize to a denatured double-stranded DNA probe comprising either the full sequence (encoding for the mature part of the polypeptide) shown in positions 88–1033 of SEQ ID NO:1, or any probe comprising a subsequence of SEQ ID NO:1, or any probe comprising a subsequence of SEQ ID NO:1 having a length of at least about 100 base pairs under at least medium stringency conditions, but preferably at high stringency conditions as described in detail below. Suitable experimental conditions for determining hybridization at medium, or high stringency between a nucleotide probe and a homologous DNA or RNA sequence involves pre-soaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5× Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), 32P-dCTP-labeled (specific activity higher than 1×109 cpm/µg) probe for 12 hours at approximately 45° C. The filter is then washed twice for 30 minutes in 2×SSC, 0.5% SDS at least 60° C. (medium stringency), still more preferably at least 65° C. (medium/high stringency), even more preferably at least 70° C. ( high stringency), and even more preferably at least 75° C. (very high stringency).

Molecules to which the oligonucleotide probe hybridizes under these conditions are detected using a x-ray film.

As previously noted, the isolated polynucleotides of the present invention include DNA and RNA. Methods for isolating DNA and RNA are well known in the art. DNA and RNA encoding genes of interest can be cloned in Gene Banks or DNA libraries by means of methods known in the art.

Polynucleotides encoding polypeptides having pectate lyase activity of the invention are then identified and isolated by, for example, hybridization or PCR.

The present invention further provides counterpart polypeptides and polynucleotides from different bacterial strains (orthologs or paralogs). Of particular interest are pectate lyase polypeptides from gram-positive alkalophilic strains, including species of Bacillus.

Species homologues of a polypeptides pectate lyase activity of the invention can be cloned using information and compositions provided by the present invention in combination with conventional cloning techniques. For example, DNA can be cloned using chromosomal DNA obtained from a cell type that expresses the protein. Suitable sources of DNA can be identified by probing Northern blots with probes designed from the sequences disclosed herein. A library is then prepared from chromosomal DNA of a positive cell line. A DNA encoding an polypeptide having pectate lyase activity of the invention can then be isolated by a variety of methods, such as by probing with a complete or partial DNA or with one or more sets of degenerate probes based on the disclosed sequences. A DNA can also be cloned using the polymerase chain reaction, or PCR (Mullis, U.S. Pat. No. 4,683,202), using primers designed from the sequences disclosed herein. Within an additional method, the DNA library can be used to transform or transfect host cells, and expression of the DNA of interest can be detected with an antibody (mono-clonal or polyclonal) raised against the pectate lyase cloned from a Bacillus species which is expressed and purified as described in Materials and Methods and the Examples, or by an activity test relating to a polypeptide having pectate lyase activity. Similar techniques can also be applied to the isolation of genomic clones.

The polypeptide encoding part of the DNA sequence cloned into plasmid pSJ1678 present in Escherichia coli DSM 12712 and/or an analogue DNA sequence of the invention may be cloned from a Bacillus strain producing the pectate lyase enzyme, or another or related organism as described herein.

Alternatively, the analogous sequence may be constructed on the basis of the DNA sequence obtainable from the plasmid present in *Escherichia coli* DSM 12712, e.g. be a sub-sequence thereof, and/or by introduction of nucleotide substitutions which do not give rise to another amino acid sequence of the pectat lyase encoded by the DNA sequence, but which corresponds to the codon usage of the host organism intended for production of the enzyme, or by introduction of nucleotide substitutions which may give rise to a different amino acid sequence (i.e. a variant of the pectate lyase of the invention).

Based on the sequence information disclosed herein a full length DNA sequence encoding a pectinase of the invention and comprising the DNA sequence shown in SEQ ID No 1 may be cloned.

Cloning of is performed by standard procedures known in the art such as by, preparing a genomic library from a Bacillus strain;plating such a library on suitable substrate plates; identifying a clone comprising a polynucleotide sequence of the invention by standard hybridization techniques using a probe based on SEQ ID No 1; or by identifying a clone from e.g. a Bacillus strain by an Inverse PCR strategy using primers based on sequence information from SEQ ID No 1. Reference is made to M. J. MCPherson et al. ("PCR A practical approach" Information Press Ltd, Oxford England) for further details relating to Inverse PCR.

Based on the sequence information disclosed herein (SEQ ID No 1 and 2) is it routine work for a person skilled in the art to isolate homologous polynucleotide sequences encoding homologous pectinases of the invention by a similar strategy using genomic libraries from related microbial organisms, in particular from genomic libraries from other strains of the genus Bacillus such as *Bacillus subtilis*.

Alternatively, the DNA encoding the pectate lyase of the invention may, in accordance with well-known procedures, conveniently be cloned from a suitable source, such as any of the below mentioned organisms, by use of synthetic oligonucleotide probes prepared on the basis of the DNA sequence obtainable from the plasmid present in *Escherichia coli* DSM 12712.

Accordingly, the polynucleotide molecule of the invention may be isolated from *Escherichia coli*, DSM 12712, in which the plasmid obtained by cloning such as described above is deposited. Also, the present invention relates to an isolated substantially pure biological culture of the strain *Escherichia coli*, DSM 12712.

POLYPEPTIDES

The sequence of amino acids no. 30–344 of SEQ ID No 2 is a mature pectate lyase sequence; positions 1–29 is a propeptide.

The present invention also provides pectate lyase polypeptides that are substantially homologous to the mature polypeptide of SEQ ID NO: 2 and its species homologs (paralogs or orthologs. The term "substantially homologous" is used herein to denote polypeptides having at least 35%, preferably at least 40%, preferably at least 45%, preferably at least 50%, preferably at least 60%, more preferably at least 70%, more preferably at least 85%, and even more preferably at least 90%, sequence identity to the sequence shown in SEQ ID NO:2 or its orthologs or paralogs. Such polypeptides will more preferably be at least 95% identical, and most preferably 98% or more identical to the sequence shown in SEQ ID NO:2 or its orthologs or paralogs. Percent sequence identity is determined by conventional methods, by means of computer programs known in the art such as GAP provided in the GCG program package (Program Manual for the Wisconsin Package, Version Aug. 8, 1994, Genetics Computer Group, 575 Science Drive, Madison, Wis. USA 53711) as disclosed in Needleman, S. B. and Wunsch, C. D., (1970), Journal of Molecular Biology, 48, 443–453, which is hereby incorporated by reference in its entirety. GAP is used with the following settings for polypeptide sequence comparison: GAP creation penalty of 3.0 and GAP extension penalty of 0.1.

Sequence identity of polynucleotide molecules is determined by similar methods using GAP with the following settings for DNA sequence comparison: GAP creation penalty of 5.0 and GAP extension penalty of 0.3.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

However, even though the changes described above preferably are of a minor nature, such changes may also be of a larger nature such as fusion of larger polypeptides of up to 300 amino acids or more both as amino- or carboxyl-terminal extensions to a pectate lyase polypeptide of the invention.

TABLE 1

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of a polypeptide according to the invention. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the pectate lyase polypeptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (i.e pectate lyase activity) to identify amino acid residues that are critical to the activity of the molecule. See also, Hilton et al., *J. Biol. Chem.* 271:4699–4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with polypeptides which are related to a polypeptide according to the invention.

Multiple amino acid substitutions can be made and tested using known methods of mutagenesis, recombination and/or shuffling followed by a relevant screening procedure, such as those disclosed by Reidhaar-Olson and Sauer (*Science* 241:53–57, 1988), Bowie and Sauer (*Proc. Natl. Acad. Sci. USA* 86:2152–2156, 1989), WO95/17413, or WO 95/22625. Briefly, these authors disclose methods for simultaneously randomizing two or more positions in a polypeptide, or recombination/shuffling of different mutations (WO95/17413, WO95/22625), followed by selecting for functional a polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223, 409; Huse, WIPO Publication WO 92/06204) and region-directed mutagenesis (Derbyshire et al., *Gene* 46:145, 1986; Ner et al., *DNA* 7:127, 1988).

Mutagenesis/shuffling methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues or entire regions in a polypeptide of interest, and can be applied to polypeptides of unknown structure.

Using the methods discussed above, one of ordinary skill in the art can identify and/or prepare a variety of polypeptides that are substantially homologous to residues 30 to 344 of SEQ ID NO:2 and retain the pectate lyase activity of the wild-type protein.

Accordingly, the present invention relates to pectate lyases having an amino acid sequence which is derived from the amino acid sequence SEQ ID No: 2 by deletion, replacement or addition of one or more amino acid residues (hereinafter referred to as mutation) provided that the pectate lyase activity is not deactivated. Also, the degree of mutation is not particularly limited. Preferably, 30% or higher homology exists between such mutation variants of the native or parent pectate lyase enzyme, calculated on the sequence SEQ ID No: 2. Preferably, the homology is at least 35%, preferably at least 40%, preferably at least 45%, preferably at least 50%, more preferably at least 55%, more preferably at least 60%, even more preferably at least 70%, even more preferably at least 75%, even more preferably at least 80%, even more preferably at least 85%, even more preferably at least 90%, even more preferably at least 95%, especially at least 98%.

For example, at the N-terminal the amino acid residue Alanine (Ala) in position 30 (when aligned in accordance with the numbering of the appended SEQ ID NO:2) may be substituted by Glutamic acid (Glu), ie A30E, and/or Glutamic acid in position 32 may be substituted by Alanine, ie E32A. These substitutions corresponds to the following changes in the coding gene, cf. SEQ ID NO:1: C89A and A95C, respectively.

The pectate lyase of the invention may, in addition to the enzyme core comprising the catalytically domain, also comprise a cellulose binding domain (CBD), the cellulose binding domain and enzyme core (the catalytically active domain) of the enzyme being operably linked. The cellulose binding domain (CBD) may exist as an integral part of the encoded enzyme, or a CBD from another origin may be introduced into the pectin degrading enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I–X), and demonstrates that CBDs are found in various enzymes such as cellulases, xylanases, mannanases, arabinofuranosidases, acetyl esterases and chitinases. CBDs have also been found in algae, e.g. the red alga *Porphyra purpurea* as a non-hydrolytic polysaccharide-binding protein, see Tomme et al., *op.cit*. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the pectin degrading enzyme and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to to about 100 amino acids, more preferably of from 2 to 40 amino acids; and X is an N-terminal or C-terminal region of the pectin degrading enzyme of the invention.

Preferably, the enzymes of the present invention have their maximum catalytic activity at a pH of at least 8, more preferably higher than 8.5, more preferably higher than 9, more preferably higher than 9.5, more preferably higher than 10, even more preferably higher than 10.5, especially higher than 11; and preferably the maximum activity of the enzyme is obtained at a temperature of at least 50° C., more preferably of at least 55° C., especially of at least 60° C.

PROTEIN PRODUCTION

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Bacterial cells, particularly cultured cells of gram-positive organisms, are preferred. Gram-positive cells from the genus of Bacillus are especially preferred, such as *Bacillus subtilis, Bacillus lentus, Bacillus brevis, Bacillus stearothermophilus, Bacillus alkalophilus, Bacillus amyloliquefaciens, Bacillus coagulans, Bacillus circulans, Bacillus clausii, Bacillus lautus, Bacillus thuringiensis, Bacillus agaradhaerens* or *Bacillus licheniformis*.

Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989; Ausubel et al. (eds.), *Current Protocols in Molecular Biology*, John Wiley and Sons, Inc., N.Y., 1987; and (Bacillus subtilis and Other Gram-Positive Bacteria, Sonensheim et al., 1993, American Society for Microbiology, Washington D.C.), which are incorporated herein by reference.

In general, a DNA sequence encoding a pectate lyase of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide into the secretory pathway of a host cell, a secretory signal sequence (also known as a leader sequence, prepro sequence or pre sequence) is provided in the expression vector. The secretory signal sequence may be that of the polypeptide, or may be derived from another secreted protein or synthesized de novo Numerous suitable secretory signal sequences are known in the art and reference is made to (*Bacillus subtilis* and Other Gram-Positive Bacteria, Sonensheim et al., 1993, American Society for Microbiology, Washington D.C.; and Cutting, S. M.(eds.) "Molecular Biological Methods for Bacillus". John Wiley and Sons, 1990) for further description of suitable secretory signal sequences especially for secretion in a Bacillus host cell. The secretory signal sequence is joined to the DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The polypeptides of the present invention may also be produced by fermenting a wildtype strain belonging to the genus Bacillus and mutants and variants derived therefrom. Such a mutant may be obtained by using conventional mutagenesis by subjecting the strain in question to treatment with a mutagen (eg NTG (n-methyl-N-nitro-N-nitrosoguanidine)) or to ultraviolet radiation, eg as described in Manual of methods for General Bacteriology; ASM 1981, Chapter 13. This mutagenesis is performed to stimulate mutation of the strains. Following mutagenesis a screening for mutants giving higher pectinase yields aer possible using conventional plate assays or liquid assays.

The fermentation may be carried out by cultivation of the strain under aerobic conditions in a nutrient medium containing carbon and nitrogen sources together with other essential nutrients, the medium being composed in accordance with the principles of the known art. The medium may be a complex rich medium or a minimal medium. The nitrogen source may be of inorganic and/or organic nature. Suitable inorganic nitrogen sources are nitrates and ammonium salts. Among the organic nitrogen sources quite a number are used regularly in fermentations. Examples are soybean meal, casein, corn, corn steep liquor, yeast extract, urea and albumin. Suitable carbon sources are carbohydrates or carbohydrate containing materials. Preferable the nutrient medium contains pectate, polygalacturonic acid and/or pectin esterified to a higher or lower degree as carbon source and/or inducer of pectinase production. Alternatively, the medium contains a pectin rich material such as soybean meal, apple pulp or citrus peel.

Since the Bacillus species producing the pectate lyases of this invention preferably are alkalophilic the cultivation is preferably conducted at alkaline pH values such as at least pH 8 or at least pH 9, which can be obtained by addition of suitable buffers such as sodium carbonate or mixtures of sodium carbonate and sodium bicarbonate after sterilisation of the growth medium.

It is contemplated that fermentation of a wildtype strain or mutant in a suitable medium can result in a yield of at least 0.5 g of pectinase protein per litre of culture broth or even at least 1 g/l or 2 g/l.

PROTEIN ISOLATION

When the expressed recombinant polypeptide is secreted the polypeptide may be purified from the growth media. Preferably the expression host cells are removed from the media before purification of the polypeptide (e.g. by centrifugation).

When the expressed recombinant polypeptide is not secreted from the host cell, the host cell are preferably disrupted and the polypeptide released into an aqueous "extract" which is the first stage of such purification techniques. Preferably the expression host cells are removed from the media before the cell disruption (e.g. by centrifugation).

The cell disruption may be performed by conventional techniques such as by lysozyme digestion or by forcing the cells through high pressure. See (Robert K. Scobes, Protein Purification, Second edition, Springer-Verlag) for further description of such cell disruption techniques.

Whether or not the expressed recombinant polypeptides (or chimeric polypeptides) is secreted or not it can be purified using fractionation and/or conventional purification methods and media.

Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers.

Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

Polypeptides of the invention or fragments thereof may also be prepared through chemical synthesis. Polypeptides of the invention may be monomers or multimers; glycosylated or non-glycosylated; pegylated or non-pegylated; and may or may not include an initial methionine amino acid residue.

TRANSGENIC PLANTS

The present invention also relates to a transgenic plant, plant part or plant cell which has been transformed with a DNA sequence encoding the pectin degrading enzyme of the invention so as to express and produce this enzyme in recoverable quantities. The enzyme may be recovered from the plant or plant part. Alternatively, the plant or plant part containing the recombinant enzyme may be used as such.

The transgenic plant can be dicotyledonous or monocotyledonous, for short a dicot or a monocot. Examples of monocot plants are grasses, such as meadow grass (blue grass, Poa), forage grass such as *festuca, lolium*, temperate grass, such as Agrostis, and cereals, e.g. wheat, oats, rye, barley, rice, sorghum and maize (corn).

Examples of dicot plants are sugar beet, solanaceous plants such as tobacco and potato, legumes, such as lupins, pea, bean and soybean, and cruciferous (family Brassicaceae), such as cauliflower, oil seed rape and the closely related model organism *Arabidopsis thaliana*.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, eg on the basis of when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are eg described by Tague et al, Plant, Phys., 86, 506, 1988.

For constitutive expression the 35S-CaMV promoter may be used (Franck et al., 1980. Cell 21: 285–294). Organ-specific promoters may eg be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a *Vicia faba* promoter from the legumin B4 and the unknown seed protein gene from *Vicia faba* described by Conrad U. et al, Journal of Plant Physiology Vol. 152, No. 6 pp. 708–711 (1998), a promoter from a seed oil body protein (Chen et al., Plant and cell physiology vol. 39, No. 9 pp. 935–941 (1998), the storage protein napA promoter from *Brassica napus*, or any other seed specific promoter known in the art, eg as described in WO 91/14772. Furthermore, the promoter may be a leaf specific promoter such as the rbcs promoter from rice or tomato (Kyozuka et al., Plant Physiology Vol. 102, No. 3 pp. 991–1000 (1993), the chlorella virus adenine methyltransferase gene promoter (Mitra, A. and Higgins, D W, Plant Molecular Biology Vol. 26, No. 1 pp. 85–93 (1994), or the aldP gene promoter from rice (Kagaya et al., Molecular and General Genetics Vol. 248, No. 6 pp. 668–674 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. *op cit* disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, *Nature*, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1.992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well-known in the art.

ENZYME PREPARATION

In the present context, the term "enzyme preparation" is intended to mean either be a conventional enzymatic fermentation-product, possibly isolated and purified, from a single species of a microorganism, such preparation usually comprising a number of different enzymatic activities; or a mixture of monocomponent enzymes, preferably enzymes derived from bacterial or fungal species by using conventional recombinant techniques, which enzymes have been fermented and possibly isolated and purified separately and which may originate from different species, preferably fungal or bacterial species; or the fermentation product of a microorganism which acts as a host cell for expression of a recombinant pectate lyase, but which microorganism simultaneously produces other enzymes, e.g. pectin lyases, proteases, or cellulases, being naturally occurring fermentation products of the microorganism, i.e. the enzyme complex conventionally produced by the corresponding naturally occurring microorganism.

The pectate lyase preparation of the invention may further comprise one or more enzymes selected from the group consisting of proteases, cellulases (endo-$\beta$-1,4-glucanases), $\beta$-glucanases (endo-$\beta$-1,3(4)-glucanases), lipases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases, transglutaminases; or mixtures thereof. In a preferred embodiment, one or more or all enzymes in the preparation is produced by using recombinant techniques, i.e. the enzyme(s) is/are monocomponent enzyme(s) which is/are mixed with the other enzyme(s) to form an enzyme preparation with the desired enzyme blend.

IMMUNOLOGICAL CROSS-REACTIVITY

Polyclonal antibodies (which are monospecific for a given enzyme protein) to be used in determining immunological cross-reactivity may be prepared by use of a purified pectate lyase enzyme. More specifically, antiserum against the pectate lyase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Use in the Detergent or Cleaning Industry

In further aspects, the present invention relates to a detergent composition comprising the pectate lyase enzyme or enzyme preparation of the invention, to a process for machine treatment of fabrics comprising treating fabric during a washing cycle of a machine washing process with a washing solution comprising the pectate lyase enzyme or enzyme preparation of the invention, and to cleaning compositions, including laundry, hard surface cleaner, personal cleansing and oral/dental compositions, comprising a pectate lyase enzyme or enzyme preparation of the invention providing superior cleaning performance, i.e. superior stain removal.

Without being bound to this theory, it is believed that the pectate lyase of the present invention is capable of effectively degrading or hydrolysing any soiling or spots containing pectins and, accordingly, of cleaning laundry comprising such soilings or spots.

The cleaning compositions of the invention must contain at least one additional detergent component. The precise nature of these additional components, and levels of incorporation thereof will depend on the physical form of the composition, and the nature of the cleaning operation for which it is to be used.

The cleaning compositions of the present invention preferably further comprise a detergent ingredient selected from a selected surfactant, another enzyme, a builder and/or a bleach system.

The cleaning compositions according to the invention can be liquid, paste, gels, bars, tablets, spray, foam, powder or granular. Granular compositions can also be in "compact" form and the liquid compositions can also be in a "concentrated" form.

The compositions of the invention may for example, be formulated as hand and machine dishwashing compositions, hand and machine laundry detergent compositions including laundry additive compositions and compositions suitable for use in the soaking and/or pretreatment of stained fabrics, rinse added fabric softener compositions, and compositions for use in general household hard surface cleaning operations. Compositions containing such carbohydrases can also be formulated as sanitization products, contact lens cleansers and health and beauty care products such as oral/dental care and personal cleaning compositions.

When formulated as compositions for use in manual dishwashing methods the compositions of the invention preferably contain a surfactant and preferably other detergent compounds selected from organic polymeric compounds, suds enhancing agents, group II metal ions, solvents, hydrotropes and additional enzymes.

When formulated as compositions suitable for use in a laundry machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components. Such compositions containing carbohydrase can provide fabric cleaning, stain removal, whiteness maintenance, softening, colour appearance, dye transfer inhibition and sanitization when formulated as laundry detergent compositions.

The compositions of the invention can also be used as detergent additive products in solid or liquid form. Such additive products are intended to supplement or boost the performance of conventional detergent compositions and can be added at any stage of the cleaning process.

If needed the density of the laundry detergent compositions herein ranges from 400 to 1200 g/litre, preferably 500 to 950 g/litre of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulphates and chlorides. A preferred filler salt is sodium sulphate.

Liquid detergent compositions according to the present invention can also be in a "concentrated form", in such case, the liquid detergent compositions according the present invention will contain a lower amount of water, compared to conventional liquid detergents. Typically the water content of the concentrated liquid detergent is preferably less than 40%, more preferably less than 30%, most preferably less than 20% by weight of the detergent composition.

Suitable specific detergent compounds for use herein are selected from the group consisting of the specific compounds as described in WO 97/01629 which is hereby incorporated by reference in its entirety.

Mannanase may be incorporated into the cleaning compositions in accordance with the invention preferably at a level of from 0.0001% to 2%, more preferably from 0.0005% to 0.5%, most preferred from 0.001% to 0.1% pure enzyme by weight of the composition.

The cellulases usable in the present invention include both bacterial or fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, J61078384 and WO96/02653 which discloses fungal cellulase produced from *Humicola insolens*, Trichoderma, Thielavia and Sporotrichum, respectively. EP 739 982 describes cellulases isolated from novel Bacillus species. Suitable cellulases are also disclosed in GB-A-2075028; GB-A-2095275; DE-OS-22 47 832 and WO95/26398.

Examples of such cellulases are cellulases produced by a strain of *Humicola insolens* (*Humicola grisea* var. thermoidea), particularly the strain Humicola insolens, DSM 1800. Other suitable cellulases are cellulases originated from *Humicola insolens* having a molecular weight of about 5 kD, an isoelectric point of 5.5 and containing 415 amino acids; and a ~43 kD endo-beta-1,4-glucanase derived from *Humicola insolens*, DSM 1800; a preferred cellulase has the amino acid sequence disclosed in PCT Patent Application No. WO 91/17243. Also suitable cellulases are the EGIII cellulases from *Trichoderma longibrachiatum* described in WO94/21801. Especially suitable cellulases are the cellulases having color care benefits. Examples of such cellulases are the cellulases described in WO96/29397, EP-A-0495257, WO 91/17243, WO91/17244 and WO91/21801. Other suitable cellulases for fabric care and/or cleaning properties are described in WO96/34092, WO96/17994 and WO95/24471.

Said cellulases are normally incorporated in the detergent composition at levels from 0.0001% to 2% of pure enzyme by weight of the detergent composition.

Preferred cellulases for the purpose of the present invention are alkaline cellulases, i.e. enzyme having at least 25%, more preferably at least 40% of their maximum activity at a pH ranging from 7 to 12. More preferred cellulases are enzymes having their maximum activity at a pH ranging from 7 to 12. A preferred alkaline cellulase is the cellulase sold under the tradename Carezyme® by Novo Nordisk A/S.

Amylases (α and/or β) can be included for removal of carbohydrate-based stains. WO94/02597, Novo Nordisk A/S published Feb. 3, 1994, describes cleaning compositions which incorporate mutant amylases. See also WO95/10603, Novo Nordisk A/S, published Apr. 20, 1995. Other amylases known for use in cleaning compositions include both α- and β-amylases. α-Amylases are known in the art and include those disclosed in U.S. Pat. No. 5,003,257; EP 252,666; WO/91/00353; FR 2,676,456; EP 285,123; EP 525,610; EP 368,341; and British Patent specification no. 1,296,839 (Novo). Other suitable amylases are stability-enhanced amylases described in WO94/18314, published Aug. 18, 1994 and WO96/05295, Genencor, published Feb. 22, 1996 and amylase variants having additional modification in the immediate parent available from Novo Nordisk A/S, disclosed in WO 95/10603, published April 95. Also suitable are amylases described in EP 277 216, WO95/26397 and WO96/23873 (all by Novo Nordisk).

Examples of commercial α-amylases products are Purafect Ox Am® from Genencor and Termamyl®, Ban®, Fungamyl® and Duramyl®, all available from Novo Nordisk A/S Denmark. WO95/26397 describes other suitable amylases : α-amylases characterised by having a specific activity at least 25% higher than the specific activity of Termamyl® at a temperature range of 25° C. to 55° C. and at a pH value in the range of 8 to 10, measured by the Phadebas® α-amylase activity assay. Suitable are variants of the above enzymes, described in WO96/23873 (Novo Nordisk). Other amylolytic enzymes with improved properties with respect to the activity level and the combination of thermostability and a higher activity level are described in WO95/35382.

Preferred amylases for the purpose of the present invention are the amylases sold under the tradename Termamyl, Duramyl and Maxamyl and or the α-amylase variant demonstrating increased thermostability disclosed as SEQ ID No. 2 in WO96/23873.

Preferred amylases for specific applications are alkaline amylases, ie enzymes having an enzymatic activity of at least 10%, preferably at least 25%, more preferably at least 40% of their maximum activity at a pH ranging from 7 to 12. More preferred amylases are enzymes having their maximum activity at a pH ranging from 7 to 12.

The amylolytic enzymes are incorporated in the detergent compositions of the present invention a level of from 0.0001% to 2%, preferably from 0.00018% to 0.06%, more preferably from 0.00024% to 0.048% pure enzyme by weight of the composition.

The term xyloglucanase encompasses the family of enzymes described by Vincken and Voragen at Wageningen University [Vincken et al (1994) Plant Physiol., 104, 99–107] and are able to degrade xyloglucans as described in Hayashi et al (1989) Plant. Physiol. Plant Mol. Biol., 40, 139–168. Vincken et al demonstrated the removal of xyloglucan coating from cellulase of the isolated apple cell wall by a xyloglucanase purified from *Trichoderma viride* (endo-IV-glucanase). This enzyme enhances the enzymatic degradation of cell wall-embedded cellulose and work in synergy with pectic enzymes. Rapidase LIQ+ from Gist-Brocades contains an xyloglucanase activity.

This xyloglucanase is incorporated into the cleaning compositions in accordance with the invention preferably at a level of from 0.0001% to 2%, more preferably from 0.0005% to 0.5%, most preferred from 0.001% to 0.1% pure enzyme by weight of the composition.

Preferred xyloglucanases for specific applications are alkaline xyloglucanases, ie enzymes having an enzymatic activity of at least 10%, preferably at least 25%, more preferably at least 40% of their maximum activity at a pH ranging from 7 to 12. More preferred xyloglucanases are enzymes having their maximum activity at a pH ranging from 7 to 12.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein or genetic engineering techniques in order to optimise their performance efficiency in the cleaning compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing metal binding sites to increase chelant stability.

Use in the Textile and Cellulosic Fiber Processing Industries

The pectate lyase of the present invention can be used in combination with other carbohydrate degrading enzymes (for instance arabinanase, xyloglucanase, pectinase) for biopreparation of fibers or for cleaning of fibers in combination with detergents. Cotton fibers consist of a primary cell wall layer containing pectin and a secondary layer containing mainly cellulose. Under cotton preparation or cotton refining part of the primary cell wall will be removed. The present invention relates to either help during cotton refining by removal of the primary cell wall. Or during cleaning of the cotton to remove residual pectic substances and prevent graying of the textile.

In the present context, the term "cellulosic material" is intended to mean fibers, sewn and unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The preparation of the present invention is useful in the cellulosic fiber processing industry for the pretreatment or retting of fibers from hemp, flax or linen.

The processing of cellulosic material for the textile industry, as for example cotton fiber, into a material ready for garment manufacture involves several steps: spinning of the fiber into a yarn; construction of woven or knit fabric from the yarn and subsequent preparation, dyeing and finishing operations. Woven goods are constructed by weaving a filling yarn between a series of warp yarns; the yarns could be two different types. Knitted goods are constructed by forming a network of interlocking loops from one continuous length of yarn. The cellulosic fibers can also be used for non-woven fabric.

The preparation process prepares the textile for the proper response in dyeing operations. The sub-steps involved in preparation are a. Desizing (for woven goods) using polymeric size like e.g. starch, CMC or PVA is added before weaving in order to increase the warp speed; This material must be removed before further processing.

b. Scouring, the aim of which is to remove non-cellulosic material from the cotton fiber, especially the cuticle (mainly consisting of waxes) and primary cell wall (mainly consisting of pectin, protein and xyloglucan). A proper wax removal is necessary for obtaining a high wettability, being a measure for obtaining a good dyeing. Removal of the primary cell wall—especially the pectins—improves wax removal and ensures a more even dyeing. Further this improves the whiteness in the bleaching process. The main chemical used in scouring is sodium hydroxide in high concentrations, up to 70 g/kg cotton and at high temperatures, 80–95° C.; and c. Bleaching; normally the scouring is followed by a bleach using hydrogen peroxide as the oxidizing agent in order to obtain either a fully bleached (white) fabric or to ensure a clean shade of the dye.

A one step combined scour/bleach process is also used by the industry. Although preparation processes are most commonly employed in the fabric state; scouring, bleaching and dyeing operations can also be done at the fiber or yarn stage.

The processing regime can be either batch or continuous with the fabric being contacted by the liquid processing stream in open width or rope form. Continuous operations generally use a saturator whereby an approximate equal weight of chemical bath per weight of fabric is applied to the fabric, followed by a heated dwell chamber where the chemical reaction takes place. A washing section then prepares the fabric for the next processing step. Batch processing generally takes place in one processing bath whereby the fabric is contacted with approximately 8–15 times its weight in chemical bath. After a reaction period, the chemicals are drained, fabric rinsed and the next chemical is applied. Discontinuous pad-batch processing involves a saturator whereby an approximate equal weight of chemical bath per weight of fabric is applied to the fabric, followed by a dwell period which in the case of cold pad-batch might be one or more days.

Woven goods are the prevalent form of textile fabric construction. The weaving process demands a "sizing" of the warp yarn to protect it from abrasion. Starch, polyvinyl alcohol (PVA), carboxymethyl cellulose, waxes and acrylic binders are examples of typical sizing chemicals used because of availability and cost. The size must be removed after the weaving process as the first step in preparing the woven goods. The sized fabric in either rope or open width form is brought in contact with the processing liquid containing the desizing agents. The desizing agent employed depends upon the type of size to be removed. For PVA sizes, hot water or oxidative processes are often used. The most common sizing agent for cotton fabric is based upon starch. Therefore most often, woven cotton fabrics are desized by a combination of hot water, the enzyme α-amylase to hydrolyze the starch and a wetting agent or surfactant. The cellulosic material is allowed to stand with the desizing chemicals for a "holding period" sufficiently long to accomplish the desizing. The holding period is dependent upon the type of processing regime and the temperature and can vary from 15 minutes to 2 hours, or in some cases, several days. Typically, the desizing chemicals are applied in a saturator bath which generally ranges from about 15° C. to about 55° C. The fabric is then held in equipment such as a "J-box" which provides sufficient heat, usually between about 55° C. and about 100° C., to enhance the activity of the desizing agents. The chemicals, including the removed sizing agents, are washed away from the fabric after the termination of the holding period.

In order to ensure a high whiteness or a good wettability and resulting dyeability, the size chemicals and other applied chemicals must be thoroughly removed. It is generally believed that an efficient desizing is of crucial importance to the following preparation processes: scouring and bleaching.

The scouring process removes much of the non-cellulosic compounds naturally found in cotton. In addition to the natural non-cellulosic impurities, scouring can remove dirt, soils and residual manufacturing introduced materials such as spinning, coning or slashing lubricants. The scouring process employs sodium hydroxide or related causticizing agents such as sodium carbonate, potassium hydroxide or mixtures thereof. Generally an alkali stable surfactant is added to the process to enhance solubilization of hydrophobic compounds and/or prevent their redeposition back on the fabric. The treatment is generally at a high temperature, 80° C.–100° C., employing strongly alkaline solutions, pH 13–14, of the scouring agent. Due to the non-specific nature of chemical processes not only are the impurities but the cellulose itself is attacked, leading to damages in strength or other desirable fabric properties. The softness of the cellulosic fabric is a function of residual natural cotton waxes. The non-specific nature of the high temperature strongly alkaline scouring process cannot discriminate between the desirable natural cotton lubricants and the manufacturing introduced lubricants. Furthermore, the conventional scouring process can cause environmental problems due to the highly alkaline effluent from these processes. The scouring stage prepares the fabric for the optimal response in bleaching. An inadequately scoured fabric will need a higher level of bleach chemical in the subsequent bleaching stages.

The bleaching step decolorizes the natural cotton pigments and removes any residual natural woody cotton trash components not completely removed during ginning, carding or scouring. The main process in use today is an alkaline hydrogen peroxide bleach. In many cases, especially when a very high whiteness is not needed, bleaching can be combined with scouring.

In the examples below it is shown that the scouring step can be carried out using the pectate lyase or pectate lyase preparation of the present invention a temperature of about 50° C.–80° C. and a pH of about 7–11, thus substituting or supplementing the highly causticizing agents. An optimized enzymatic process ensures a high pectin removal and full wettability.

Degradation or Modification of Plant Material

The enzyme or enzyme preparation according to the invention is preferably used as an agent for degradation or modification of plant cell walls or any pectin-containing material originating from plant cells walls due to the high plant cell wall degrading activity of the pectate lyase of the invention.

The pectate lyase of the present invention may be used alone or together with other enzymes like glucanases, pectinases and/or hemicellulases to improve the extraction of oil from oil-rich plant material, like soy-bean oil from soy-beans, olive-oil from olives or rapeseed-oil from rape-seed or sunflower oil from sunflower.

The pectate lyase of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions, The separation process may be performed by use of methods known in the art.

The pectate lyase of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearance of processed fruit or vegetables. The consistency and appearence has been shown to be a product of the actual combination of enzymes used for processing, i.e. the specificity of the enzymes with which the pectate lyase of the invention is combined. Examples include the production of clear juice e.g. from apples, pears or berries; cloud stable juice e.g. from apples, pears, berries, citrus or tomatoes; and purees e.g. from carrots and tomatoes.

The pectate lyase of the invention may be used in modifying the viscosity of plant cell wall derived material. For instance, the pectate lyase may be used to reduce the viscosity of feed which contain pectin and to promote processing of viscous pectin containing material. The viscosity reduction may be obtained by treating the pectin containing plant material with an enyme preparation of the invention under suitable conditions for full or partial degradation of the pectin containing material.

The pectate lyase can be used e.g. in combination with other enzymes for the removal of pectic substances from plant fibres. This removal is essential e.g. in the production of textile fibres or other cellulosic materials. For this purpose plant fibre material is treated with a suitable amount of the pectate lyase of the invention under suitable conditions for obtaining full or partial degradation of pectic substances associated with the plant fibre material.

Animal Feed Additive

Pectate lyases of the present invention may be used for modification of animal feed and may exert their effect either in vitro (by modifying components of the feed) or in vivo. the pectate lyase is particularly suited for addition to animal feed compositions containing high amounts of arabinogalactans or galactans, e.g. feed containing plant material from soy bean, rape seed, lupin etc. When added to the feed the pectate lyase significantly improves the in vivo break-down of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by pectate lyase, e.g. in combination with $\beta$-galactosidase, to galactose or galactooligomers which are digestible by the animal and thus contribute to the available energy of the feed. Also, by the degradation of galactan the pectate lyase may improve the digestibility and uptake of non-carbohydrate feed constituents such as protein, fat and minerals.

For further description reference is made to PCT/DK 96/00443 and a working example herein.

Wine and Juice Processing

The enzyme or enzyme preparation of the invention may be used for de-pectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme or enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production.

DETERMINATION OF CATALYTIC ACTIVITY OF PECTATE LYASE

The Lyase Assay (at 235 nm)

For determination of the $\beta$-elimination an assay measuring the increase in absorbance at 235 nm was carried out using the substrate 0.1% polygalacturonic acid sodium salt (Sigma P-1879) solubilised in 0.1 M Glycin buffer pH 10. For calculation of the catalytic rate an increase of 5.2 Absorbency at 235 units per min corresponds to formation of 1 $\mu$mol of unsaturated product (Nasuna and Starr (1966) J. Biol. Chem. Vol 241 page 5298–5306; and Bartling, Wegener and Olsen (1995) Microbiology Vol 141 page 873–881).

Steady state condition using a 0.5 ml cuvette with a 1 cm light path on a HP diode array spectrophotometer in a temperature controlled cuvette holder with continuous measurement of the absorbency at 235 nm. For steady state a linear increase for at least 200 sec was used for calculation of the rate. It was used for converted to formation $\mu$mol per min product.

Agar Assay

Pectate lyase activity can be measured by applying a test solution to 4 mm holes punched out in agar plates (such as, for example, LB agar), containing 0.7% w/v sodium polygalacturonate (Sigma P 1879). The plates are then incubated for 6 h at a particular temperature (such as, e.g., 750° C.). The plates are then soaked in either (i) 1M CaCl2 for 0.5 h or (ii) 1% mixed alkyl trimethylammonium Br (MTAB, Sigma M-7635) for 1 h. Both of these procedures cause the precipitation of polygalacturonate within the agar. Pectate lyase activity can be detected by the appearance of clear zones within a background of precipitated polygalacturonate. Sensitivity of the assay is calibrated using dilutions of a standard preparation of pectate lyase.

Determination of Trans Units Endpoint analysis—Transelimination at 235 nm for Pectate Lyases (0.34 mM Calcium in the Final Incubation Mixture)

In this method, the substrate and enzyme is incubated for 20 min at 37° C. followed by measurement at 235 nm of the formation of double bounds. Finally, the rate of the degradation is calculated based on the molar extinction coefficient in terms of Trans Units.

Procedure:

Mixing of 0.5 ml enzyme dilution with 0.5 ml 2*substrate solution.

Substrate: Polygalacturonic acid from Sigma P-1879 lot 77H3784

Buffer 2x: 0.1M Glycin pH 10+0.8 mmol $CaCl_2$

Stop reagent: 0.02 M $H_3PO_4$

Temperature of incubation 37° C.

Reaction time 20 min.

Extinction coefficient of the transelimination 0.0052 μmol $cm^{-1}$.

Enzyme diluted in ion-free water to 0.1 to 0.4 Trans units per ml.

Main value in duplicate 0.5 ml. The 2% w/v substrate in 2x buffer is mixed with 0.5 ml diluted enzyme. Both pre-incubated 5 min on water bath at 37° C. Incubate for 20 min. Stop using 5 ml stop reagent and mix. Blank mix enzyme and stop reagent first and then ad substrate all in the same volume.

| | |
|---|---|
| Enzyme | 0.5 ml |
| Substrate | 0.5 ml |
| Stop | 5 ml |
| Total volume | 6 ml |

Measure the absorbency at 235 nm in a 1 cm cuvette.

Calculate the formation of transelimination per min using the extinction coefficient of 0.0052 μmole cm-1

Calculation: [(main plus main)/2-Blank] 0,0052*6*2*Enzyme dilution/20 min/1000 ml=μmol per min.

MATERIALS AND METHODS

Strains

*E.coli* DSM 12712 comprises the plasmid containing the pectate lyase encoding DNA sequence of the invention presented in SEQ ID NO:1.

*B.subtilis* PL2306. This strain is the *B.subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from Bacillus brevis. J. Bacteriol., 172, 4315–4321) disrupted in the transcriptional unit of the known *Bacillus subtilis* cellulase gene, resulting in cellulase negative cells. The disruption was performed essentially as described in ( Eds. A. L. Sonenshein, J. A. Hoch and Richard Losick (1993) *Bacillus subtilis* and other Gram-Positive Bacteria, American Society for microbiology, p.618).

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296–304.

For gene library in *E.coli* the used host was *Escherichia coli* SJ2 (Diderichsen, B. et al., (1990)).

Plasmids pSJ1678:

The gene bank vector was pSJ1678 which is further disclosed in WO94/19454 which is hereby incorporated by reference in its entirety.

pMOL944:

This plasmid is a pUB110 derivative essentially containing elements making the plasmid propagatable in *Bacillus subtilis*, kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell.

The plasmid was constructed by means of conventional genetic engineering techniques which are briefly described in the following.

Construction of pMOL944:

The pUB110 plasmid (McKenzie, T. et al., 1986, Plasmid 15:93–103) was digested with the unique restriction enzyme NciI. A PCR fragment amplified from the amyL promoter encoded on the plasmid pDN1981 (P. L. Jørgensen et al.,1990, Gene, 96, p37–41.) was digested with NciI and inserted in the NciI digested pUB110 to give the plasmid pSJ2624.

The two PCR primers used have the following sequences:

LWN5494 5'-GTCGCCGGGGCGGCCGCTAT CAATTGGTAACTGTATCTCAGC-3'

LWN5495 5'-GTCGCCCGGGAGCTCTGATCAG GTACCAAGCTTGTCGACCTGCAGAATG AGGCAGCAAGAAGAT-3'

The primer #LWN5494 inserts a NotI site in the plasmid.

The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670.

This cloning replaces the first amyL promoter cloning with the same promoter but in the opposite direction. The two primers used for PCR amplification have the following sequences:

LWN5938 5'-GTCGGCGGCCGCTGATCACGTAC CAAGCTTGTCGACCTGCAGAATGAGGCAGC AAGAAGAT-3'

LWN5939 5'-GTCGGAGCTCTATCAATTGGTAAC TGTATCTCAGC-3'

The plasmid pSJ2670 was digested with the restriction enzymes PstI and BclI and a PCR fragment amplified from a cloned DNA sequence encoding the alkaline amylase SP722 (disclosed in the International Patent Application published as WO95/26397 which is hereby incorporated by reference in its entirety) was digested with PstI and BclI and inserted to give the plasmid pMOL944. The two primers used for PCR amplification have the following sequence:

LWN7864 5'-AACAGCTGATCACGACTGATCTTT TAGCTTGGCAC-3'

LWN7901 5'-AACTGCAGCCGCGGCACATCATAA TGGGACAAATGGG-3'

The primer #LWN7901 inserts a SacII site in the plasmid.

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers (e.g. restriction endonucleases, ligases etc. are obtainable from New England Biolabs, Inc.).

Media
  TY (as described in Ausubel, F. M. et al. (eds.) "Current protocols in Molecular Biology". John Wiley and Sons, 1995).
  LB agar (as described in Ausubel, F. M. et al. (eds.) "Current protocols in Molecular Biology". John Wiley and Sons, 1995).
  LBPG is LB agar supplemented with 0.5% Glucose and 0.05 M potassium phosphate, pH 7.0
  BPX media is described in EP 0 506 780 (WO 91/09129).

The following non-limiting examples illustrate the invention.

EXAMPLE 1

Preparation and Screening of a Bacillus sp. Gene Library

A Bacillus sp. strain was propagated in liquid TY medium. After 18 hours incubation at 37° C. and 300 rpm, the cells were harvested, and genomic DNA isolated by the method described by Pitcher et al. (Pitcher, D. G., Saunders, N. A., Owen, R. J. (1989).

Chromosomal DNA from Bacillus sp. was partial digested with the restriction enzyme Sau3AI. The fragments were cloned into the BamHI site of the cloning vector pSJ1678 and transformed by electroporation, using a Gene Pulser™ electroporator from BIO-RAD as described by the supplier, into *Escherichia coli* SJ2 (Diderichsen, B. et al., (1990)), thereby creating a gene library of Bacillus sp.

Screening of Bacillus sp. Gene Libary for Nucleotide Sequences Encoding Pectinase Activities A Bacillus sp. library was screened by fluorescence polarisation using fluorescently labelled pectin. The labeling strategy comprised labeling of the carboxylic acid groups of pectin/polygalacturonic acids by coupling a hydrazine or amine activated probe (e.g. fluorescein-5-thiosemicarbazide) to the carboxylic acids using 1-ethyl-3-(dimethylaminopropyl) carbodiimide hydrochloride (FLUKA, Switzerland) as a mediator.

The polygalacturonic acid with a degree of esterification of 3% (1 g) was dissolved in 25 ml of demineralized water and subsequently 20 mg of fluorescein-5-thiosemicarbazide (Molecular Probes, OR, USA) was applied while stirring. The pH was adjusted to 5.9 with 1 M NaOH and (1 g) 1-ethyl-3-(dimethylaminopropyl) carbodiimide hydrochloride was added gradually over 1 h while stirring. The solution was then incubated overnight in darkness. 10% acetic acid (v/v) was added to the solution followed by addition of methanol to a final concentration of 75% (v/v) methanol. This solution was placed in darkness for 1 h. The precipitated pectin was subsequently collected by filtration on 2 layers of Miracloth (Calbiochem, Germany) and washed with acetic acid:ethanol (1:19 v/v), ethanol (96%) and finally with acetone. The labeled pectin was dried in darkness. The degree of labeling were between 0.3 and 0.7%.

Screening of the library was done as follows, the library was inoculated into 46 microtitter plates with an average of 2.1 clones per well making up a total of approximately 9500 clones. The clones were grown in LB medium with 10 $\mu$g/ml chloramphenicol for 60 hours at 37° C. with shaking (275 rpm) in a closed humidified chamber. Upon outgrowth, 50 $\mu$l of the master cell culture was transfered and mixed with 150 $\mu$l assay mix in black microtitter plates using an automated pipetting station. The assay mix consisted of 34 $\mu$g/ml apple pectin DE 3% trace labelled fluorescein (as described above), 2 mM $CaCl_2$ and 100 mM glycin buffer at pH 10. The microtitter plates were incubated at ambient temperature for 2 hours prior to being read by a fluorescence polarisation reader (Polarstar, BMG, Germany). The fluorescence polarisation value of substrate was significantly lower in two wells indicating the presence of pectinase activity. From the masterplates, two clones were purified which encoded a pectinase gene.

Sequencing of the Gene Encoding a Pectate Lyase

Standard dideoxy sequencing methods were employed on plasmid template using an ABI 373 automated sequencer. A combination of restriction subcloning and primer walking was employed to determine the sequence of the gene.

The DNA sequence is SEQ ID NO.:1 and the derived amino acid sequence is SEQ ID No.:2.

EXAMPLE 2

Cloning, Expression, Purification and Characterization of a Pectate Lyase from Bacillus sp.

Genomic DNA preparation

Strain Bacillus sp. was propagated in liquid TY medium. After 18 hours incubation at 37° C. and 300 rpm, the cells were harvested, and genomic DNA isolated by the method described by Pitcher et al. (Pitcher, D. G., Saunders, N. A., Owen, R. J. (1989). Rapid extraction of bacterial genomic DNA with guanidium thiocyanate. Lett. Appl. Microbiol., 8, 151–156).

The pectate lyase (vide supra, represented by amino acid sequence SEQ ID NO:2) encoding DNA sequence of the invention was PCR amplified using the PCR primer set consisting of these two oligo nucleotides:

Pecl.B.sp.upper.SacII

5'-CAT TCT GCA GCC GCG GCA GCA GAA GAA GCA ACG GTT TCC AAC G-3'

Pecl.B.sp.lower.NotI

5'-GCG TTG AGA CGC GCG GCC GCT CAT TAA CGA AGC TTT TGC GGC C-3'

Restriction sites SacII and NotI are underlined.

Chromosomal DNA isolated from Bacillus sp. as described above was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 $\mu$M of each dNTP, 2.5 units of AmpliTaq polymerase (Perkin-Elmer, Cetus, USA) and 100 pmol of each primer.

The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-$\mu$l aliquots of the amplification product was analysed by electrophoresis in 0.7% agarose gels (NuSieve, FMC). The appearance of a DNA fragment size 1.0 kb indicated proper amplification of the gene segment.

Subcloning of PCR Fragment

Fortyfive-$\mu$l aliquots of the PCR products generated as described above were purified using QIAquick PCR purification kit (Qiagen, USA) according to the manufacturer's instructions. The purified DNA was eluted in 50 $\mu$l of 10 mM Tris-HCl, pH 8.5. 5 $\mu$g of pMOL944 and twentyfive-$\mu$l of the purified PCR fragment was digested with SacII and NotI, electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment was then ligated to the SacII-NotI digested and purified pMOL944. The ligation was performed overnight at 16° C. using 0.5 μg of each DNA fragment, 1 U of T4 DNA ligase and T4 ligase buffer (Boehringer Mannheim, Germany).

The ligation mixture was used to transform competent *B.subtilis* PL2306. The transformed cells were plated onto LBPG-10 μg/ml of Kanamycin plates. After 18 hours incubation at 37° C. several clones were restreaked on fresh agar plates and also grown in liquid TY cultures with 10 μg/ml kanamycin and incubated overnight at 37° C. Next day 1 ml of cells were used to isolate plasmid from the cells using the Qiaprep Spin Plasmid Miniprep Kit #27106 according to the manufacturers recommendations for *B.subtilis* plasmid preparations. This plasmid DNA was used as template for DNA sequencing.

One clone containing the pectate lyase gene was kept, this clone was termed MB939.

The DNA corresponding to the mature part of the pectate lyase was characterised by DNA sequencing by primerwalking, using the Taq deoxy-terminal cycle sequencing kit (Perkin-Elmer, USA), fluorescent labelled terminators and appropriate oligonucleotides as primers.

Analysis of the sequence data was performed according to Devereux et al. (1984) Nucleic Acids Res. 12, 387–395. The cloned DNA sequence is represented in SEQ ID NO: 1. The cloned DNA sequence was expressed in *B.subtilis* and the protein that appeared in the supernatant corresponded to the mature protein represented in SEQ ID NO:2.

Purification

MB939 was grown in 15×200 ml BPX media with 10 μg/ml of Kanamycin in 500 ml two baffled shakeflasks for 5 days at 37° C. at 300 rpm, whereby 2500 ml of culture broth was obtained. The pH was adjusted to 6.1, using acetic acid and 25 ml of cationic agent (C521 10%) and 60 ml of anionic agent (A130 0.1%) was added during agitation for flocculation. The flocculated material was separated by centrifugation using a Sorval RC 3B centrifuge at 10000 rpm for 30 min at 6° C. The resulting supernatant contained 820 Trans units per ml in a total volume of 2400 ml.

The supernatant was clarified using Whatman glass filters GF/D and C and finally concentrated on a filtron UF membrane with a cut off of 10 kDa. The total volume of 500 ml was adjusted to pH 8.0.

For obtaining a highly purified pectate lyase a final step using Q-sepharose anion-exchange chromatography was carried out. 500 ml of the solution of total 1,362,420 Trans units was applied to a 800 ml column containing Q-Sepharose (Pharmacia) equilibrated with a buffer of 50 mmol Tris pH 8.0. The pectate lyase bound and was eluted using a 0.5 M NaCl gradient.

Characterisation

The pure enzyme constitutes a single band in SDS-PAGE of 36 kDa and has an isoelectric point of about 5.6.

The protein concentration was determined using a molar extinction coefficient of 80510 (based on the amino acid composition deducted from the sequence).

The activity could be inhibited by EDTA. However, as long as the EDTA concentration did not exceed the Ca concentration more than 75% of relative activity could be obtained (cf. Table 1b). The enzyme was not further activated by increasing the calcium concentration (cf. Table 1a).

The pH dependency of activity showed more than 50% relative activity between pH 8.5 and 11.0 at 37° C. (cf. Table 2). The temperature optima at pH 10 was 60° C. (cf. Table 3).

Differential Scanning Calorimetry DSC of the pure enzyme revealed a melting temperature of 58.8° C. at pH 8 in 0.1 M Tris buffer.

TABLE 1a

The relative activity at different levels of Ca (at pH 10, 50 mM glycine buffer; substrate 1% polygalacturonic acid)

| $CaCl_2$ mmol | % activity |
| --- | --- |
| 0.00 | 27 |
| 0.20 | 79 |
| 0.40 | 85 |
| 0.60 | 80 |
| 0.80 | 88 |
| 1.00 | 100 |

TABLE 1b

The relative activity at different levels of EDTA + 0.38 mmol $CaCl_2$ (at pH 10, 50 mM glycine buffer; substrate 1% polygalacturonic acid)

| EDTA mmol | % activity |
| --- | --- |
| 0.00 | 100 |
| 0.10 | 83 |
| 0.20 | 73 |
| 0.30 | 50 |
| 0.40 | 0 |
| 1.00 | 0 |

TABLE 2

The relative activity (rate) is calculated as percentage of the optimum activity; substrate 1% polygalacturonic acid

| pH | % activity |
| --- | --- |
| 6.9 | 6 |
| 7.4 | 17 |
| 7.9 | 33 |
| 8.4 | 33 |
| 8.5 | 66 |
| 9.3 | 83 |
| 9.8 | 92 |
| 10.1 | 100 |
| 10.7 | 96 |

TABLE 3

The relative activity at different temperatures (at pH 10, 50 mM glycine buffer; substrate 1% polygalacturonic acid)

| temp. ° C. | % activity |
| --- | --- |
| 37 | 27 |
| 50 | 61 |
| 60 | 100 |
| 70 | 4 |
| 80 | 1 |

LITERATURE

Lever, M. (1972) A new reaction for colormetric determination of carbohydrates. Anal. Biochem. 47, 273–279.

N. C. Carpita and D. M. Gibeaut (1993) The Plant Journal 3:1–30.

Diderichsen, B., Wedsted, U., Hedegaard, L., Jensen, B. R., Sjøholm, C. (1990) Cloning of aldb, which encodes alpha-acetolactate decarboxylase, an exoenzyme from *Bacillus brevis*. J. Bacteriol. 172:4315–4321.

What is claimed is:

1. An isolated polypeptide
   (a) having an amino acid sequence that is at least 70% identical to the sequence of amino acid residues 30–344 of SEQ ID NO: 2: or
   (b) encoded by a DNA sequence that hybridizes with the sequence of nucleotides 88–1033 of SEQ ID NO:1 under medium stringency conditions; wherein the polypeptide has pectate lyase activity.

2. The polypeptide of claim 1, which has an amino acid sequence that is at least 70% identical to the sequence of amino acid residues 30–344 of SEQ ID NO: 2 and is encoded by a DNA sequence that hybridizes with the sequence of nucleotides 88–1033 of SEQ ID NO: 1 under medium stringency conditions.

3. The polypeptide of claim 1, which has an amino acid sequence that is at least 70% identical to the sequence of amino acid residues 30–344 of SEQ ID NO: 2.

4. The polypeptide of claim 3, which has an amino acid sequence that is at least 85% identical to the sequence of amino acid residues 30–344 of SEQ ID NO: 2.

5. The polypeptide of claim 4, which has an amino acid sequence that is at least 90% identical to the sequence of amino acid residues 30–344 of SEQ ID NO: 2.

6. The polypeptide of claim 5, which has an amino acid sequence that is at least 95% identical to the sequence of amino acid residues 30–344 of SEQ ID NO: 2.

7. The polypeptide of claim 6, which has an amino acid sequence that is at least 98% identical to the sequence of amino acid residues 30–344 of SEQ ID NO: 2.

8. The polypeptide of claim 1, which comprises an amino acid sequence of amino acid residues 30–344 of SEQ ID NO: 2 or a fragment thereof.

9. The polypeptide of claim 1, which consists of an amino acid sequence of amino acid residues 30–344 of SEQ ID NO: 2.

10. The polypeptide of claim 1, which is encoded by a DNA sequence that hybridizes with the sequence of nucleotides 88–1033 of SEQ ID NO: 1 under medium stringency conditions.

11. The polypeptide of claim 10, which is encoded by a DNA sequence that hybridizes with the sequence of nucleotides 88–1033 of SEQ ID NO: 1 under high stringency conditions.

12. The polypeptide of claim 1, which is endogenous to a strain of the genus Bacillus.

13. The polypeptide of claim 1, which is encoded by the DNA sequence contained in plasmid pSJ1678 in *Escherichia coli* DSM 12712.

14. The polypeptide of claim 1, which does not belong to polysaccharide family 1, 2 and 9.

15. A fusion protein comprising a polypeptide of claim 1, that is linked to one or more cellulose binding domains (CBD).

16. An enzyme preparation comprising a polypeptide of claim 1.

17. The preparation of claim 16, which further comprises one or more enzymes selected from the group consisting of alpha-amylases, arabinosidases, cellobiohydrolases, cellulases (endoglucanases), cutinases, galactases, beta-glucanases, glucoamylases, hemicellulases, laccases, ligninases, lipases, mannanases, oxidases pectate lyases, pectin acetyl esterases, pectinases, pectin lyases, pectin methylesterases, peroxidases, phenoloxidase, polygalacturonases, proteases, pullulanases, reductases, rhamnogalacturonases, transglutaminases, xylanases, and xyloglucariases.

18. A detergent composition comprising a polypeptide of claim 1 and a surfactant.

19. A process for cleaning a hard surface, comprising treating a hard surface with a cleaning solution comprising a polypeptide of claim 1.

20. A process for machine treatment of a fabric, comprising treating the fabric during a washing cycle of a machine washing process with a washing solution comprising the polypeptide of claim 1.

21. A method for improving the properties of cellulosic fibers, yarn, woven or non-woven fabric, comprising treating the fibers, yarn or fabric with an effective amount of the polypeptide of claim 1.

22. The method of claim 21, wherein the polypeptide is used in a scouring process step.

23. A method for degradation or modification of a plant material, comprising treating the plant material with an effective amount of the polypeptide of claim 1.

24. The method of claim 23, wherein the plant material is recycled waste paper, mechanical paper-making pulps or fibers subjected to a retting process.

25. A method for preparing animal feed, comprising adding an effective amount of the polypeptide of claim 11 to animal feed ingredients.

26. A method for processing wine or juice, comprising treating the wine or juice with an effective amount of the polypeptide of claim 1.

* * * * *